United States Patent
Sha et al.

(10) Patent No.: US 6,420,621 B2
(45) Date of Patent: *Jul. 16, 2002

(54) OPTIMIZED PROCESS FOR THE PREPARATION OF OLEFINS BY DIRECT CONVERSION OF MULTIPLE HYDROCARBONS

(75) Inventors: Yingxun Sha; Zhongqiang Cui; Guoliang Wang; Mingdang Wang, all of Luoyang (CN)

(73) Assignees: China Petro-Chemical Corp., Beijing; Luoyang Petrochemical Engineering Corporation SINOPEC, Luoyang, both of (CN)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/174,462

(22) Filed: Oct. 19, 1998

(30) Foreign Application Priority Data

Oct. 20, 1997 (CN) .......................................... 97119048 A

(51) Int. Cl.⁷ .......................... C07C 4/06; C10G 11/00; C10G 11/02
(52) U.S. Cl. ........................ 585/653; 585/650; 585/921; 585/923; 208/113; 208/118; 208/120.01
(58) Field of Search ................................ 585/650, 653, 585/921, 923; 208/113, 118, 120.01, 130

(56) References Cited

U.S. PATENT DOCUMENTS

| 4,087,350 A | 5/1978 | Kolombos et al. ........... 208/121 |
| 4,242,100 A | * 12/1980 | Parker et al. .................. 44/53 |
| 4,259,177 A | 3/1981 | Ueda et al. .................. 208/127 |
| 4,291,185 A | * 9/1981 | Kaeding ...................... 585/467 |
| 4,320,241 A | * 3/1982 | Frankiewicz ................. 585/469 |
| 4,422,925 A | * 12/1983 | Williams et al. ............... 208/75 |
| 4,663,019 A | 5/1987 | Gartside et al. ............... 208/50 |
| 4,670,021 A | * 6/1987 | Nelson et al. .................. 44/66 |
| 4,693,991 A | * 9/1987 | Bjornson et al. ........... 502/220 |
| 5,173,174 A | * 12/1992 | Upson et al. ................ 208/120 |
| 5,264,115 A | 11/1993 | Mauleon et al. .............. 208/67 |
| 5,348,644 A | * 9/1994 | Maroy et al. ................ 208/153 |
| 5,382,349 A | * 1/1995 | Yoshita et al. ................. 208/49 |
| 5,506,365 A | 4/1996 | Mauleon et al. ............ 585/329 |

FOREIGN PATENT DOCUMENTS

| CN | 88102644.1 | 2/1989 |
| CN | 89100052.6 | 8/1989 |
| CN | 92105507.2 | 2/1993 |
| EP | 0 381 870 | 8/1990 |

OTHER PUBLICATIONS

European Search Report issued in European Patent No. EP 98 11 9730.

\* cited by examiner

Primary Examiner—Thuan D. Dang
(74) Attorney, Agent, or Firm—Pennie & Edmonds LLP

(57) ABSTRACT

A process for hydrocarbon conversion to prepare lower olefins such as ethylene, propylene, etc., and light aromatics by bringing hydrocarbons into contact with a solid granular catalyst. In order to optimize the reaction conditions and product structure and save the capital and operating costs, a piston flow reactor is used in this process and multiple groups of feed inlets, which allow hydrocarbons with different properties to enter the device from different feed inlets and proceed pyrolysis under different operation conditions, are set on the reactor. This process is usable for individual pyrolysis or co-feed pyrolysis of hydrocarbons from refinery gases, liquid hydrocarbons, to heavy residues.

5 Claims, 1 Drawing Sheet

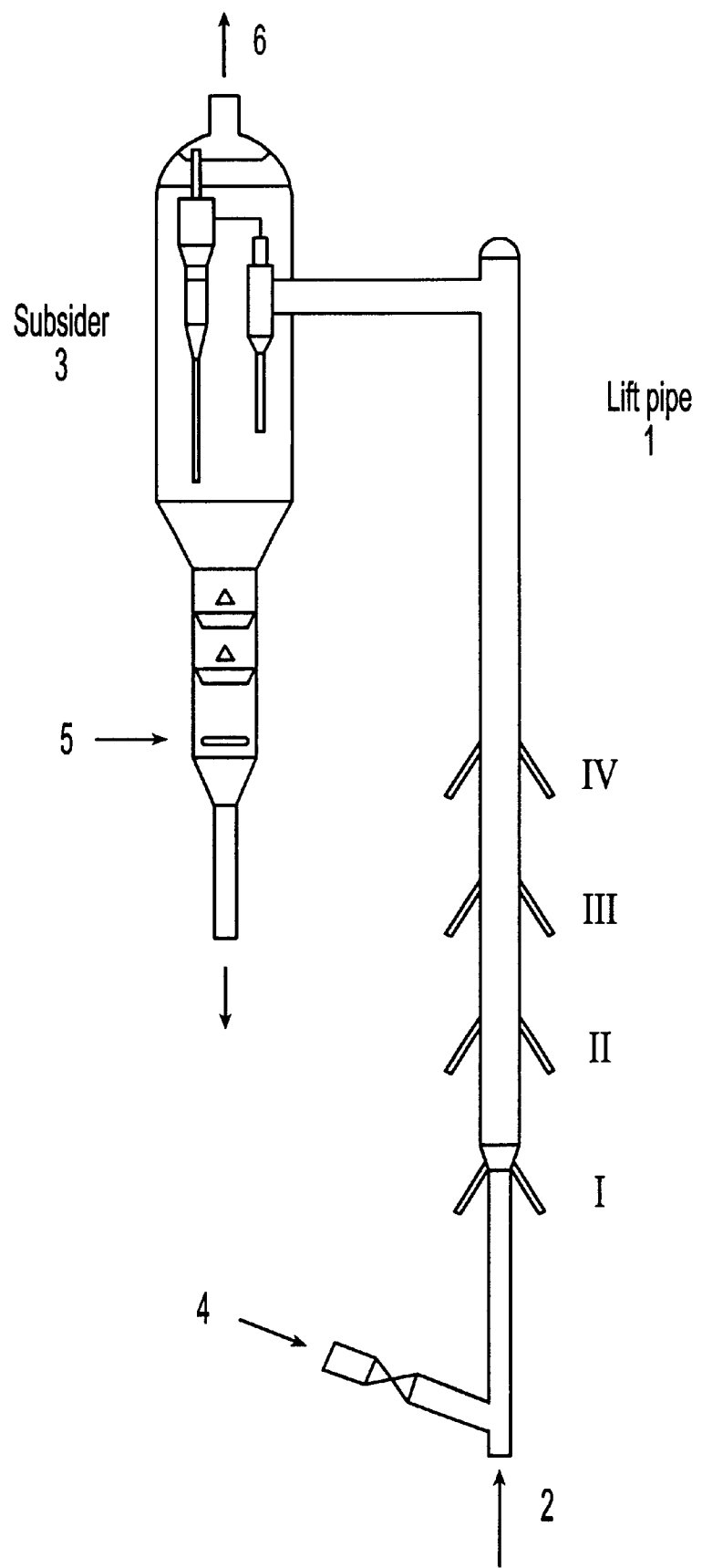

OPTIMIZED PROCESS FOR THE PREPARATION OF OLEFINS BY DIRECT CONVERSION OF MULTIPLE HYDROCARBONS

FIELD OF THE INVENTION

The present invention relates to a technological process for the preparation of lower olefins with stress on ethylene by conversion of hydrocarbons.

BACKGROUND ARTS

Research on the production of ethylene by the pyrolysis of heavy oils has been very active in recent years both in china and abroad, for example, the QC (quick contact) reaction system developed by Stone & Webster Eng Co. of USA (U.S. Pat. No. 4,663,019, ZL88102644.1 and EP 0381870A etc.): this technology uses a downward tubular reactor and a feeding mode of a single feed oil. The steam pyrolysis technology developed by British Petroleum Ltd. (U.S. Pat. No. 4,087,350): this technology uses a tubular fixed bed catalytic reactor. The technology developed by Tokyo Science and Technology Co. of Japan for producing olefins using coke particles as a heat carrier (U.S. Pat. No. 4,259,177): this technology uses a fluidized bed reactor of the reaction-regeneration type. The HCC (Heavy-oil contact cracking) technology developed by SINOPEC Loyang Petro-Chemical Engineering Co. (ZL 92105507.2): this technology uses an up flow or down flow tubular piston flow reactor and a feeding mode of a single feed oil. The above technologies are all able to produce ethylene from heavy oils. But in the flow sheets of the above technologies, only the case of feeding a single fresh feed oil is considered. American patent U.S. Pat. No. 5,348,644 is patent for an invention relating to the improvement of the feeding equipment and technological process of a lift pipe catalytic cracking device. The fluidization state of the catalyst in the lift pipe is optimized by installation of special equipment in the pre-lift section of the lift pipe and thereby the contact state of the catalyst and the feed oil for the catalytic cracking in the lift pipe is improved and more ideal product distribution of the catalytic cracking is obtained. Chinese patent ZL 8910052, U.S. Pat. No. 5,264,115 and U.S. Pat. No. 5,506,365 provide a fluidized bed process and device for converting hydrocarbons which consists of a steam pyrolysis section for light hydrocarbon fractions at the upstream of a reaction zone and a catalytic cracking section for heavy hydrocarbon fractions at the downstream of said reaction zone in a tubular reaction zone with an upstream or downstream flow in the presence of the catalyst particles in a fluidized phase. The applied catalyst belongs to the type of catalytic cracking. The purpose is to obtain a propylene yield slightly higher than the conventional catalytic cracking while raising the yields of gasoline and diesel oil in the product. The major characteristic is to separate $C_2$ components from the product and then introduce them into an oligomerization reactor to proceed the oligomerization reaction; the remained $C_2$ components and the oligomerization products are returned to the lift pipe to proceed the steam cracking reaction so that the purpose of raising the yields of fuel oils and propylene is achieved. It can be seen from the example that the yields of the $C_2$ olefin, $C_3$ olefin in this technology are both lower than 7.0% by weight.

In order to solve the problems of simultaneous feeding of multiple feed oils and/or re-refining of some pyrolyzed by-products (e.g etheane, propane etc) in the technology of heavy oil pyrolysis to prepare ethylene, the present invention is to provide an effective method which allows different feed conduct the proylsis under different process conditions so that optimizing the reaction conditions and product structure, raising the yield of ethylene and saving the capital and operation costs can be realized.

The major characteristic of the present invention is the multiple feed accompanied by ethane re-refining for the purpose of producing more ethylene. In the technological process for conversion of hydrocarbons to prepare gaseous olifins by bringing them into contact with solid catalyst particles, the feed hydrocarbons are not only one and the desired pyrolysis conditions for various hydrocarbons are not completely the same. For example, the optimal reaction temperature for ethane is higher than that for naphtha and the optimal reaction temperature for naphtha is highter than that for vacuum distillates, and so on. In order to pyrolyze various feed hydrocarbons under their respective optimal conditions as far as possible, separate heaters are used in the tubular heater pyrolysis technology. For example, there must be one or two ethane pyrolysis heaters to proceed pyrolysis for re-refining ethane in the plant that uses naphtha or light diesel oil as a feed. In the technology of the catalytic pyrolysis for ethylene preparation, it is impossible to pyrolyze the feeds with different properties in separate heaters because there is only one reactor. The optimal pyrolysis conditions can not be met for various hydrocarbons if they are mixed and then fed. Taking the simultaneous pyrolysis of an atmospheric residue and ethane as an example, the optimal pyrolysis temperature for the atmospheric residue (at the outlet) is 650–750° C., but the pyrolysis rate of ethane in this temperature range can not meet the need of industrial production; if the pyrolysis temperature is raised to above 800° C. to meet the conditions for ethane pyrolysis, the pyrolysis extent of the atmospheric residue can not be controlled. In the above case, it is possible to feed the atmospheric residue and ethane separately and attain desired pyrolysis extents for various feeds by using the method of the multiple feed at separate points of the present invention.

SUMMERY OF THE INVENTION

One aspect of the present invention is therefore to provide a process for catalytic pyrolysis of hydrocarbon feeds to produce lower olefins with stress on ethylene and co-produce light aromatics, which is to bring the hydrocarbon feeds into contact with a solid granular catalyst in a piston flow reactor to proceed catalytic pyrolysis, the hydrocarbon feeds include two or more hydrocarbons having different physicochemical properties, the feed hydrocarbons are mixed with steam and introduced, the general reaction conditions in the reaction zone are: temperature 600–900° C., pressure 0.13–0.40 MPa (absolute), total steam/hydrocarbon ratio 0.1–1.0, total catalyst/oil ratio 5–100 and the catalyst/oil contact time 0.02–5 s; the oil gas after reaction is separated quickly from the catalyst and quenched, the catalyst is recycled for reuse after regeneration, different feeds are introduced from different positions, hydrocarbons difficult to pyrolyze are first introduced into the reactor and brought into contact with the catalyst of high temperatures and high activities from the regenerator and the pyrolysis takes place, meanwhile, the catalyst cools down and deactivates; then other hydrocarbons easier to pyrolyze are introduced in sequence from the upstream to downstream of the reaction zone, the hydrocarbons introduced later play a role of quenching those introduced earlier, the temperature of the reaction zone and the activity of the catalyst are lowered step by step from the upstream to the downstream; the positions from which various hydrocarbons enter the reactor are determined as such that the residence times of various hydrocarbons in the reactor are gradually decreased in the sequence from difficulty to ease in pyrolysis, the differences in the residence times of every adjacent two hydrocarbon feeds in the reactor are 0.01–3 s.

Another aspect of the present invention is to provide a process for direct conversion of heavy hydrocarbons to produce lower olefins with stress on ethylene and co-produce light aromatics, which is to bring the hydrocarbon feeds into contact with a solid granular catalyst in a piston flow reactor to proceed catalytic pyrolysis, the feed hydrocarbons are mixed with steam and introduced, the general reaction conditions in the reaction zone are: temperature 600–900° C., pressure 0.13–0.40 MPa (absolute), total steam/hydrocarbon ratio 0.1–1.0, total catalyst/oil ratio 5–100 and the catalyst/oil contact time 0.02–5 s; the oil gas after reaction is separated quickly from the catalyst and quenched, the catalyst is recycled for reuse after regeneration; the oil gas enters a fractionation and separation system to proceed the separation, a product gas mainly containing ethylene, the by-product ethane, and a liquid product rich in aromatics can be obtained, the highly pure by-product ethane from the separation system and/or the gases containing ethane from other sources return to the pyrolysis reactor of the piston flow type from the upstream inlet of the reactor and come into contact with the catalyst of high temperatures and high activities, fast pyrolysis takes place at temperatures higher than 780° C. to produce ethylene and meanwhile, the catalyst cools down and deactivates, steam is introduced at the same time when ethane feed is introduced from the upstream inlet of the reactor; heavy hydrocarbon feeds are introduced at position certain distance from downstream of the inlet for ethane, the hydrocarbons introduced later play a role of quenching those introduced earlier, the reaction temperature at this moment is lowered to 680–800° C.; the feeding positions of the by-product ethane and the heavy hydrocarbons are determined as such that the residence time of ethane, which is difficult to pyrolyze, is long, while that of heavy hydrocarbons, which are easy to pyrolyze, is short, the differences in the residence times of ethane and heavy hydrocarbons in the reactor are 0.01–3 s.

BRIEF DESCRIPTION OF THE DRAWING

The FIGURE—Schematic diagram of the lift pipe reactor of the present invention as an example 1-Lift pipe
2-Pre-lift gas
3-Subsider
4-Regenerated catalyst
5-Pipeline for stripping steam
6-Outlet of the pyrolyzed gas
I, II, III, IV are all the feed inlets

DETAILED DESCRIPTION OF THE INVENTION

Hydrocarbons entering the reactor from different inlets are subjected to different reaction conditions, for light hydrocarbons, which are difficult to pyrolyze, the pyrolysis temperature is higher and the pyrolysis time is longer, while for heavy hydrocarbons, which are difficult to pyrolyze, the reaction temperature is lower and the pyrolysis time is shorter. Hydrocarbons with different properties are fed to the reactor in sequence and the differences in the residence times in the reactor of adjacent hydrocarbons are 0.0–3 s. Hydrocarbons hard to pyrolyze are first fed to the reactor and brought into contact with the catalyst of high temperatures and high activities from the regenerator and the pyrolysis reaction takes place, at the same time, the catalyst cools down and deactivates and then other hydrocarbon feeds easy to pyrolyze are fed in sequence, the hydrocarbons fed later play a role of quenching those fed earlier.

This method is usable for the technology in which one or multiple hydrocarbon oil(s) are used as the feed(s), said hydrocarbons include ethane, propane, butane, light hydrocarbons and heavy hydrocarbons. Said heavy hydrocarbons are referred to the hydrocarbons with a distillation range higher than 350° C., including straight run heavy hydrocarbons and secondary processing heavy hydrocarbons, i.e., various straight run wax oils, coker wax oils, straight run vacuum gas oils, atmospheric residues, coker gas oils, thermal cracking heavy oils, solvent-deasphalted oils and various solvent extraction residues of heavy hydrocarbons; said light hydrocarbons are referred to hydrocarbons with a distillation range lower than 350° C., such as LPG, refinery petroleum gases, oil field gases, oil field light hydrocarbons, naphtha and light diesel oil.

Citing a lift pipe reactor as an example, the particular process is described as follows (see The FIGURE): the regenerated catalyst 4 from the regenerator enters the lift pipe 1, and then flows upward under the driving of the pre-lifting steam and pre-lifting dry gas introduced from the bottom of the lift pipe; the pre-lifting dry gas is highly pure ethane from the separation zone of the pyrolyzed gas and/or light hydrocarbon gases of other sources containing ethane, steam is added at the same time; ethane quickly pyrolyzes under the action of the hot catalyst at 780–900° C., ethane may also be sprayed from inlet I. A mixture of propane and/or butane from the separation zone and/or other sources and a certain amount of steam is atomized and sprayed from feed inlet II into the lift pipe, where the mixture comes into contact with the mixed stream of the catalyst and the ethane reactant at about 780–850° C. and the catalytic pyrolysis reaction takes place. A mixture of the light hydrocarbons having a distillation range lower than 350° C. and a certain amount of steam is atomized and sprayed from feed inlet II into the lift pipe, where the mixture comes into contact with the mixture of the catalyst and the upstream reactants at 720–830° C. and the catalytic pyrolysis reaction takes place. A mixture of heavy hydrocarbons having a distillation range higher than 350° C. and a certain amount of steam is atomized and sprayed from feed inlet IV into the lift pipe, where the mixture comes into contact with the mixture of the catalyst and the upstream reaction stream at about 680–800° C. and the catalytic pyrolysis reaction takes place. The distances among the feed inlets for various hydrocarbons are calculated to allow the differences in the residence time of the adjacent hydrocarbons introduced into the reactor in sequence to be 0.0–3 s. Heavier feed oils are sprayed in sequence into the lift pipe at the inlets above the inlets from which the lighter feed oils are sprayed and may play a role of quenching the pyrolyzed stream of lighter feed oils so that the secondary reactions of the pyrolyzed stream of the lighter feed oils are quickly stopped or slowed down. The mixture of the catalyst and the reaction stream of the hydrocarbon feeds in the lift pipe flows upward and enters the subsider 3, wherein fast separation of gas/solid stream is performed. The reaction stream is removed from the outlet 6 at the top of the subsider, while the deactivated catalyst drops down along the subsider and is stripped by the stripping steam sprayed from the pipeline 5. The stripped catalyst to be regenerated goes down and enters the regenerator, wherein the coke-burning regeneration reaction is carried out, the regeneration temperature being 700–950° C. During the coke-burning regeneration, the catalyst absorbs a great amount of heat and its temperature rises to 800–900° C. After steam stripping in the transfer pipeline, the high temperature regenerated catalyst is recycled back to the pre-lift section of the lift pipe along the regeneration inclined pipe for reuse. After quenching, the reaction stream removed from exit 6 enters the fractionation system and separates into pyrolyzed gas and a liquid product rich in aromatics, the pyrolyzed gas is then separated in the separation system into highly pure individual hydrocarbons ($CH_4$, $C_2H_4$, $C_2H_6$, $C_3H_6$, $C_3H_8$, $C_4H_8$, $C_4H_6$, $C_4H_{10}$), wherein the highly pure ethane returns to be bottom of the lift pipe for pyrolysis or is delivered to the ethane pyrolysis heater for pyrolysis.

The components of the special catalyst (LCM) used for the catalytic pyrolysis can be selected from $SiO_2$, $Al_2O_3$ and oxides of alkali metals, alkali earth metals and transition metals or mixtures thereof, aluminum silicate modified with oxides of alkali or alkali earth metals can also be used, and optionally, a part of molecular sieves are added.

If the feed hydrocarbon to be pyrolyzed are two or more in the scope of ethane, propane, butane, light hydrocarbons having a distillation range lower than 350° C. and heavy hydrocarbons having a distillation range higher than 350° C., different feeds can enter the device from different positions according to the above method to realize the optimization of the pyrolysis conditions.

The effect of the present invention. Realization of the pyrolysis of the feeds with different properties under different process conditions results in the optimization of the reaction conditions and product structure, e.g., the yield of ethylene attains 23.76 wt % or higher, as well as savings of capital and operating costs.

EXAMPLE 1

This example is the pyrolysis results using an atmospheric residue and ethane as a co-feed. The pyrolysis test is carried out on a high-low parallel lift pipe pilot-scale device with a total length of the lift pipe being 15.42 m, its internal diameter being 19 mm and a capacity being 0.24 t/d. Ethane, which is difficult to pyrolyze, is first introduced into the lift pipe from the bottom of the lift pipe and brought into contact with the hot and active regenerated catalyst so that reaction takes place, the temperature of the regenerated catalyst at this moment is 820° C., the temperature of the hydrocarbon/catalyst mixture after introducing ethane is 810° C. The inlet of the atmospheric residue is located 4.2 m above the inlet of ethane. The residence time of ethane from the bottom to this point is 0.45 s. The temperature of the mixed stream after introducing the atmospheric residue is 740° C., the temperature at the outlet of the lift pipe is 710° C. The catalyst used in this example is numbered as LCM-A, its properties and composition are shown in Table 1. The process conditions and the material balance in a pilot-scale test of the lift pipe are shown in Table 2. For comparison, the result of the pilot-scale test is also shown when the atmospheric residue and ethane is mixed and fed from the same inlet.

The results in Table 2 show that, in the technology of ethylene production from atmospheric residues with ethane re-refining, rather optimal pyrolysis conditions for both the atmospheric residue and ethane are realized and the conversions are appropriate when the method of multiple feed at separate point of the present invention are adopted. The yield of ethylene from the individual pyrolysis of the atmospheric residue is 22.36 wt %, while that after the re-refining of 4.56% of ethane attains 25.63 wt %.

It can also be seen from Table 2 that when the pyrolyzed ethane from the atmospheric residue is not re-refined and additional 6.5 wt % ethane is added, if ethane and the heavy oil are fed from the same feed inlet and the temperature of catalyst/oil mixture is 740° C., the yield of ethylene is only 21.30%; if ethane and the heavy oil are fed into the device from different feed inlets, i.e., the temperature at the inlet for ethane is 810° C. and that for the residue is 740° C., the yield of ethylene is 23.76%. Moreover, the aromatic content in the pyrolyzed gasoline is greater than 86 wt %, that in the pyrolyzed liquid product having a distillation range higher than 200° C. is greater than 89 wt %.

EXAMPLE 2

This example is the pyrolysis results using an atmospheric residue and a straight run gasoline as a co-feed, the process conditions and the material balance in a pilot-scale test of the lift pipe are shown in Table 3. The straight run gasoline is introduced into the device from the bottom of the lift pipe, the number of the catalyst used is LCM-B, its propertied and composition are seen in Table 1. The temperature of the catalyst/oil mixture is 780° C., the atmospheric residue is sprayed at the position 4.2 m above the inlet of the straight run gasoline, the residence time of the straight run gasoline from the bottom to this point is 0.6 s, and the temperature of the mixed stream after spraying the atmospheric reside is 700° C., the temperature at the outlet of the lift pipe is 660° C.

The results in Table 3 show that, by using the method of mixed feed of the atmospheric residue and the straight run gasoline, the total pyrolysis extent of the mixed feed is rather low when the optimal conditions for the pyrolysis of the atmospheric residue are ensured, in the total material balance, the yields of ethylene and propylene are 21.84% and 12.93%, respectively, either of them is lower than that when only the atmospheric reside is pyrolyzed, indicating that the pyrolysis extent of the straight run gasoline is not high; rather high pyrolysis extent of the straight run gasoline is attained while ensuring that the pyrolysis of the atmospheric residue proceeds under the optimal conditions by using the method of the multiple feed at separate point of the present invention: in the total material balance of the mixed feed, the yield of ethylene reaches 24.50%, that of propylene reaches 14.51%, either of them exceeds that when only the atmospheric residue is pyrolyzed.

TABLE 1

Properties and composition of the catalyst

| Item<br>Type of the active component | Catalyst LCM-A<br>Alkali<br>earth metal Oxides | Catalyst LCM-B<br>Transition metal<br>oxides |
|---|---|---|
| Chemical composition | | |
| $Al_2O_3$, wt % | 40 | 42 |
| $Na_2O$, wt % | <0.3 | <0.3 |
| $Fe_2O_3$, wt % | 0.8 | 0.8 |
| Active component, wt % | 8.2 | 6.5 |
| Specific surface, $m^2/g$ | 58 | 65 |
| Porosity, ml/g | 0.12 | 0.13 |
| Bulk density, g/ml | 0.85 | 0.85 |

TABLE 1-continued

Properties and composition of the catalyst

| Item<br>Type of the active component | Catalyst LCM-A<br>Alkali<br>earth metal Oxides | Catalyst LCM-B<br>Transition metal<br>oxides |
|---|---|---|
| Sieve composition, wt % | | |
| 0–20 μ | 2.6 | 3.2 |
| 20–40 μ | 19.4 | 20.2 |
| 40–60 μ | 31.5 | 32.1 |
| 60–80 μ | 24.7 | 23.9 |
| >80 μ | 21.8 | 20.6 |

TABLE 2

Pyrolysis result using ethane and an atmospheric residue

| Item | Material balance for the pyrolysis of the atmospheric residue | | Material balance for the pyrolysis of the atmospheric residue and ethane | |
|---|---|---|---|---|
| Feeding mode | Single | Separate* | Mixed | Separate |
| Whether ethane is refined | No | Yes | No | No |
| Ethane content in feed, wt % | 0.0 | 0.0 | 6.5 | 6.5 |
| Temp. of regeneration bed, ° C. | 820 | 820 | 820 | 820 |
| Temp. of stripping steam for regenerated catalyst, ° C. | 400 | 400 | 400 | 400 |
| Stream temp. after spraying ethane, ° C. | / | 810 | 740 | 810 |
| Stream temp. after spraying atmospheric residue, ° C. | 740 | 740 | 740 | 740 |
| Temp. at the outlet of lift pipe, ° C. | 710 | 710 | 710 | 710 |
| Temp. after quenching, ° C. | 600 | 600 | 600 | 600 |

TABLE 2-continued

Pyrolysis result using ethane and an atmospheric residue

| Item | Material balance for the pyrolysis of the atmospheric residue | | Material balance for the pyrolysis of the atmospheric residue and ethane | |
|---|---|---|---|---|
| Feeding mode | Single | Separate* | Mixed | Separate |
| Catalyst type | A | A | A | A |
| Steam/hydrocarbon ratio, wt/wt | 0.23 | 0.23 | 0.23 | 0.23 |
| Catalyst/oil ratio, wt/wt | 18.0 | 18.0 | 18.0 | 10 |
| Yield of major products, wt % | | | | |
| Hydrogen | 0.87 | 1.09 | 0.84 | 1.03 |
| Methane | 11.44 | 11.81 | 10.76 | 11.13 |
| Ethylene | 22.36 | 25.63 | 21.30 | 23.76 |
| Ethane | 4.56 | / | 10.20 | 6.79 |
| Propylene | 12.86 | 13.25 | 12.05 | 12.21 |
| Propane | 0.71 | 0.72 | 0.67 | 0.68 |
| Butane | 0.22 | 0.22 | 0.21 | 0.21 |
| Butylene | 3.04 | 3.10 | 2.85 | 2.90 |
| Butadiene | 1.87 | 1.91 | 1.75 | 1.76 |
| Pyrolyzed gasoline (<200° C.) | 12.46 | 12.76 | 11.68 | 11.85 |
| Pyrolyzed middle distillate | 5.23 | 5.24 | 4.94 | 4.89 |
| Pyrolyzed heavy oil (>300° C.) | 9.86 | 9.88 | 9.30 | 9.22 |
| Coke | 13.23 | 13.27 | 12.40 | 12.37 |
| Loss | 1.29 | 1.12 | 1.05 | 1.21 |
| Where: (1) Aromatic content in pyrolyzed gasoline | 88.12 | 87.75 | 86.54 | 87.87 |
| (2) Aromatic content in the pyrolyzed product having a distillation range higher than 200° C. | 90.13 | 89.89 | 90.10 | 91.39 |

*Ethane in the pyrolyzed product from the atmospheric residue is returned back to the lift pipe for re-refining.

TABLE 3

Pyrolysis result using straight run gasoline and an atmospheric residue

| Item | Material balance for the pyrolysis of atmospheric residue | Material balance for pyrolysis of straight run gasoline | Material balance for pyrolysis of atmospheric residue and straight run gasoline | |
|---|---|---|---|---|
| Feeding mode | Single | Single | Mixed | Separate |
| Gasoline proportion in feed, wt % | 0.0 | 100 | 20 | 20 |
| Temp. of regeneration bed, ° C. | 800 | / | 800 | 800 |
| Temp. of stripping steam for regenerated catalyst, ° C. | 400 | / | 400 | 400 |
| Stream temp. after spraying gasoline, ° C. | / | 780 | 700 | 780 |
| Stream temp. after spraying atmospheric residue, ° C. | 700 | 700 | 700 | 700 |
| Temp. at the outlet of the lift pipe, ° C. | 660 | 660 | 660 | 660 |
| Temp. after quenching, ° C. | 600 | 600 | 600 | 600 |
| Catalyst type | B | B | B | B |
| Steam/hydrocarbon ratio, wt/wt | 0.25 | / | 0.25 | 0.25 |
| Catalyst/oil ratio, wt/wt | 18.6 | / | 19.2 | 19.0 |
| Yield of major products, wt % | | | | |
| Ethylene | 23.05 | 30.30 | 21.84 | 24.50 |
| Propylene | 14.01 | 16.51 | 12.93 | 14.51 |
| C$_4$ olefins | 6.73 | 8.48 | 6.24 | 7.08 |
| Pyrolyzed gasoline (<200° C.) | 13.45 | 19.20 | 23.16 | 14.60 |
| Pyrolyzed middle distillate | 6.60 | 2.00 | 5.50 | 5.68 |
| Pyrolyzed heavy oil (>300° C.) | 9.31 | 0.01 | 7.45 | 7.45 |
| Coke plus loss | 9.00 | 0.50 | 7.30 | 7.30 |
| Where: (1) Aromatic content in pyrolyzed gasoline | 88.44 | 92.30 | 78.52 | 89.10 |
| (2) Aromatic content in the pyrolyzed product having a distillation range higher than 200° C. | 92.65 | / | 92.50 | 93.76 |

What is claimed is:

1. A process for direct conversion of heavy hydrocarbon with a distillation range higher than 350° C. with steam to produce lower olefins mainly being ethylene and light aromatics, which comprises:

(a) mixing and bringing into contact the heavy hydrocarbon feed with steam and a solid granular catalyst in the reaction zone of a piston flow reactor having a single lift pipe to proceed catalytic pyrolysis, thereby forming an oil gas, wherein the catalyst comprising $AL_2O_3$ and/or $SiO_2$ and an active component selected from the group consisting of oxides of alkali metals, alkali earth metals, transition metals and mixtures thereof, and aluminum silicate modified with oxides of alkali or alkali earth metals; and wherein conditions in the reaction zone are: temperature 600–900° C., pressure 0.13–40 MPa (absolute), total steam/hydrocarbon ratio 0.1–1.0 wt/wt, total catalyst/oil ratio 5–100 wt/wt and the catalyst contact time 0.02–5 s; and (b) separating quickly the oil gas from the catalyst after reactions and quenching the oil gas, wherein the catalyst is recycled for reuse after regeneration; and the oil gas enters a fractionation and separation system to proceed the separation, wherein a product gas mainly containing ethylene, propylene, bytene, butadiene, the by-product ethane, and a liquid product rich in aromatics is obtained; the highly pure by-product ethane from the sepatation system and/or the gases containing ethane from other sources return to the pyrolysis reactor of the piston flow from the upstream inlet of the reactor and come into contact with the catalyst of higher temperatures and high activities, fast pyrolysis takes place at temperatures higher than 780° C. to produce ethylene and meanwhile, the catalyst cools down and deactivates, steam is introduced at the same time when ethane feed is introduced from the upstream inlet of the reactor; heavy hydrocarbon feed is introduced at position certain distances from downstream of the inlet for ethane, the hydrocarbon introduced later plays a role of quenching those introduced earlier, the reaction temperature at this moment is 680–800° C.; the feeding positions of the ethane and the heavy hydrocarbon are determined as such that the residence time of ethane, which is difficult to pyrolyze, is long, while that of heavy hydrocarbon, which are easy to pyrolyze, is short, the differences in the residence times of ethane and heavy hydrocarbons in the reactor are 0.001–3 s.

2. A process according to claim 1, wherein the heavy hydrocarbon is straight run heavy hydrocarbons and secondary processing heavy hydrocarbons.

3. A process according to claim 1, wherein the deactivated catalyst is delivered to the regenerator for regeneration by burning off the coke after steam stripping, the regeneration temperature is 750–900° C, the high temperature regenerated catalyst is drawn after steam stripping and recycled back to the reactor through an inclined lift pipe for reuse.

4. A process for catalytic pyrolysis according to claim 1 wherein the lower olefin is ethylene, propylene, butene and butadiene.

5. A process for catalytic pyrolysis according to claim 2, wherein the straight run and secondary processing heavy hydrocarbons are selected from the group consisting of straight run wax oils, coker wax oils, straight run vacuum gas oils, atmopheric residues, coker gas oils, thermal heavy oils, solvent-deasphalted oils and various residues from solvent extraction of heavy hydrocarbons.

* * * * *